United States Patent [19]

Lazarus

[11] Patent Number: 4,720,264

[45] Date of Patent: Jan. 19, 1988

[54] DUAL TORQUE LIMITING AND WINDING TOOL

[76] Inventor: Harry J. Lazarus, 36 Knox La., Englishtown, N.J. 07724

[21] Appl. No.: 25,003

[22] Filed: Mar. 12, 1987

[51] Int. Cl.$^4$ ............................................. A61C 5/04
[52] U.S. Cl. ..................................................... 433/39
[58] Field of Search ........................... 433/39, 141, 40

[56] References Cited

U.S. PATENT DOCUMENTS 3,411,214 11/1968 Lazarus ................................. 433/39
3,852,884 10/1974 Lazarus ................................. 433/39

Primary Examiner—Robert Peshock
Attorney, Agent, or Firm—McGlew and Tuttle

[57] ABSTRACT

A winding tool for winding a coil of a retainerless dental matrix comprising a rotatable handle having a handle bore therethrough. A nonrotatable palm grip is mounted on a shaft for axial movement into the handle. A barrel having a torque transmitting mechanism is mounted for rotation and for axial movement in the handle. The torque limiting mechanism is transmitted and interengages the barrel to the handle for transmitting limited torque applied by rotating the handle for rotating the barrel and activating said torque limitor which rotates. A bent flexible sleeve which is fixed to an end of the barrel. A winding head is fixed to a remote end of the flexible sleeve. A compression transmitting shaft having a bent end extending into the bent flexible sleeve for retaining the bent shape thereof extends through the barrel and into the palm grip where it is fixed against rotation with the palm grip. A biasing spring which forms a part of the torque transmitting mechanism is compressed by the shaft which yieldingly permits the barrel and torque transmitting mechanism to be rotated over the shaft without requiring rotation of the shaft. The winding head also has a truncated conical shape and deep flutes having cutting edges for engaging the coil of the retainerless dental matrix.

20 Claims, 19 Drawing Figures

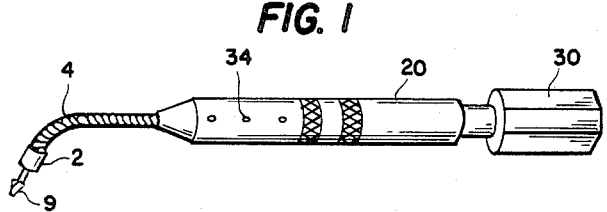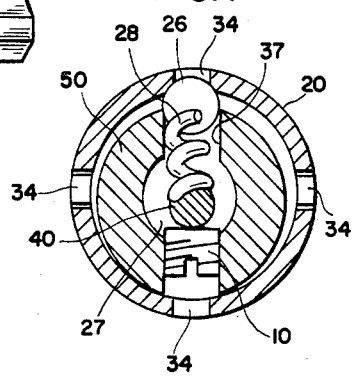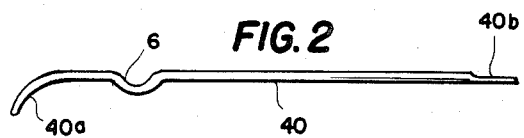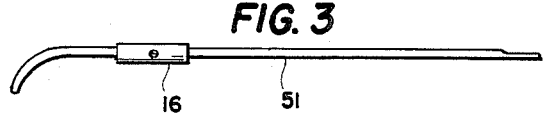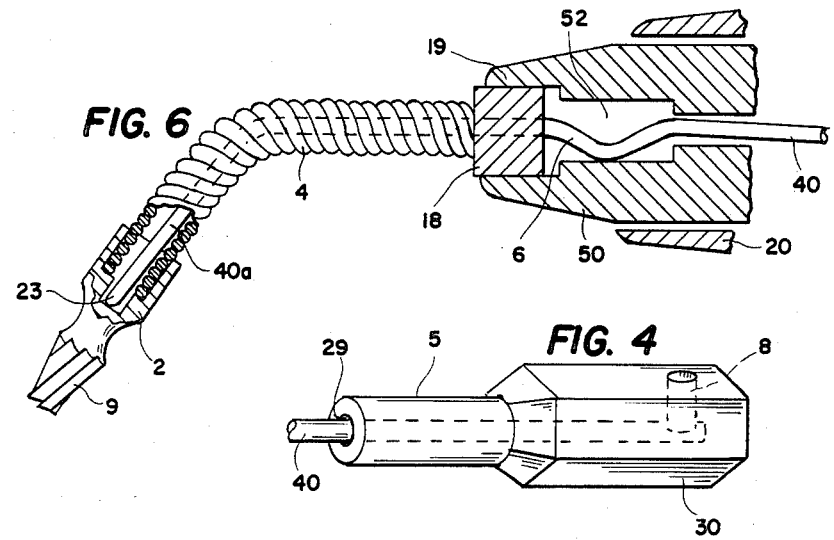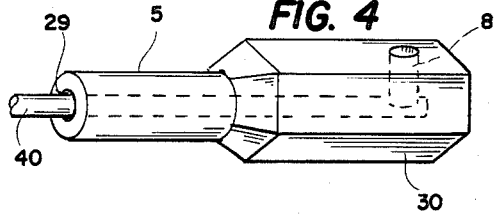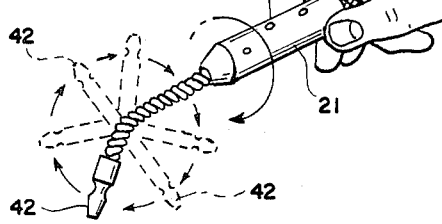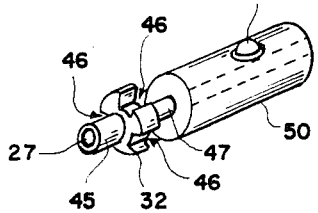

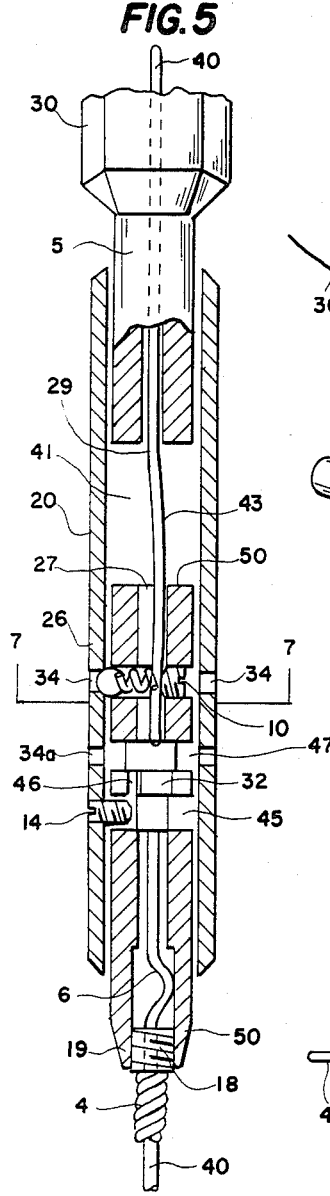
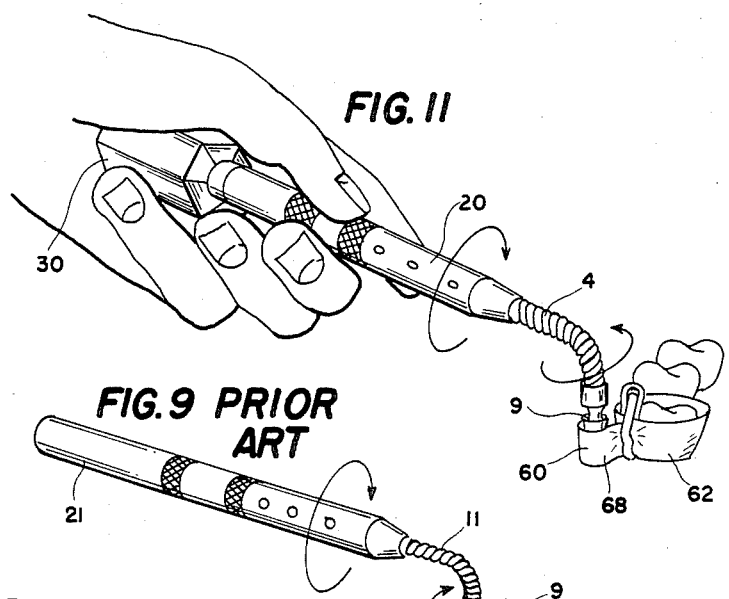
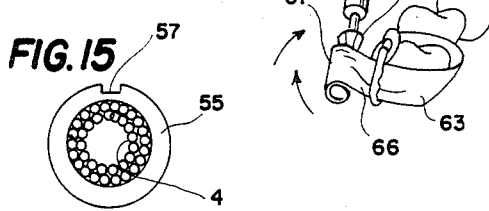
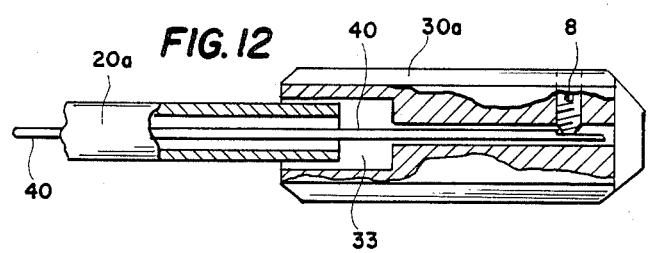
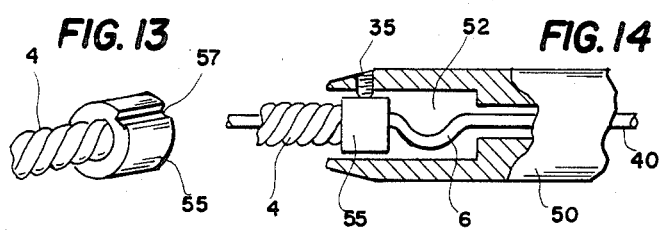
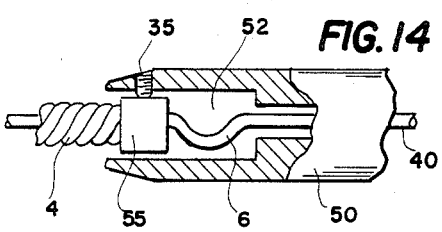

DUAL TORQUE LIMITING AND WINDING TOOL

FIELD AND BACKGROUND OF THE INVENTION

The invention relates in general to a winding and tightening tool which is used for tightening a preformed coil of a self-locking retainerless dental matrix.

A winding tool of this type was introduced by the present inventor in his previous U.S. Pat. No. 3,435,905 issued Apr. 1, 1969 and entitled Tool and Method of Manufacturing the Same, hereinafter referred to as the -905 patent. This tool was improved further by the present inventor as disclosed in his U.S. Pat. No. 3,852,884 issued Dec. 10, 1974 and entitled Winding and Tightening Tool and Method of Manufacturing Same, hereinafter referred to as the -884 patent.

These tools were used to wind the preformed coil of a metal dental matrix disclosed by the inventor in his U.S. Pat. No. 3,411,214, issued Nov. 19, 1968, entitled Dental Appliance, hereinafter referred to as the -214 patent and his U.S. Pat. No. 3,921,299 issued Nov. 25, 1985 and entitled Retainerless Dental Matrix and Method of Manufacture, hereinafter referred to as the -299 patent. The -905 patent did not provide a torque limiting means, while the -884 patent provided a single torque limitor, suitable for limiting torque on a steel matrix only.

A plastic retainerless matrix was also introduced by the inventor in his U.S. Pat. No. 4,523,909 issued June 18, 1985 and entitled Plastic Dental Matrix and Method of Manufacturing Same, hereinafter referred to as the -909 patent.

To provide a tool having two separate torque limitors, one being a high torque limitor for tightening a steel matrix and another low torque limitor for tightening the plastic matrix, the present inventor disclosed a winding tool having two different torque limiting means and means for selecting the required limitor for either the metal or plastic matrix winding coil. This was disclosed in the inventor's U.S. Pat. No. 4,551,097 issued Nov. 5, 1985 and entitled Dual-Torque Winding and Tightening Tool, hereinafter referred to as the -097 patent (which patents are all incorporated here by reference).

The object of the tool torque limiting and winding tool was to provide, in a single tool, the capacity of winding the coil of the metal matrix with higher limiting torque and for winding the coil of the plastic matrix with lower limiting torque. Particularly in the case of the plastic matrix, the tearable coil could easily be damaged by exerting too much torque. With the destruction or deformation of the winding coil, the matrix could no longer be tightened and would thus not function correctly. The torque limitor of the -097 patent prevents tearing of the coil.

However, an additional problem which was not fully addressed by the -097 patent dual torque limiting and winding tool was in the tool's disability to freely disengage the winding head or member from the coil after the coil had been tightened.

It has been found that the winding head often tends to remain bound within the plastic coil when tool is reversely wound for disengagement from said coil. This makes it difficult to extricate the winding head from the coil after the matrix has been tightened. Failure to disengage is related to an undesirable "propellering" of the tool's flexible sleeve and winding head.

Referring to FIGS. 8 and 9, FIG. 8 illustrates the tendency of the winding head 42 to rotate like a propeller when the handle 21 of the winding tool is rotated reversely in the hand. When the winding head 42 of the prior tool is seated in a coil, and wound to tighten the coil this propellering motion does not occur, because the winding coil is pressed against the tooth which supports the coil against propellering. Propellering occurs only when the reverse wind is used to disengage the winding head from the coil, as the reverse winding direction draws the coil away from the tooth, losing the support which prevents propellering.

Absent said support during reverse winding for disengagement of the tool the winding head tends to move in propeller-like fashion shown in FIG. 8, causing destructive twisting of the coil without routinely effecting disengagement.

As shown in FIG. 9, it has been found that when a dentist rotates the handle 21 in an opposite direction in an attempt to remove the winding head 9 from a plastic winding coil 61, the propellering action tends to twist and deform the coil 61 out and away from the matrix 63 and away from the tooth carrying matrix. The flexible sleeve 11 which carries the winding head 9 attempts to move in propeller-like fashion as illustrated in FIG. 8. The resulting deformation of the winding coil and part of the matrix not only makes it even more difficult to remove the winding head from the winding coil but also tends to loosen the matrix 63, rendering it useless for its intended purpose.

To try to avoid this propellering action of the flexible sleeve 11 when using the tool with a plastic matrix, and during said reverse winding of the tool, dentists have been applying a finger of the hand which is not operating the winding tool and pressing this finger against the side of the winding coil 61 toward the tooth to effect an anti-propellering hold to the reversely wound coil, while the winding head is thus disengaged and removed axially from the coil. Propellering occurs only with plastic bands, as the steel matrix is stiffer and resists the propellering. This procedure is of course awkward since the dentist must reach into the patient's mouth, and position the finger over the rotating tool to reach the coil. Using the finger to hold the winding coil against propellering also obscures the dentist's field of vision, as well as cluttering the operative field. This tends to discourage the use of the finger technique, which results in the undesired deformation and destruction of the coil and matrix as illustrated in FIG. 9.

One feature of the plastic matrix was to fasten, in the coil core a staple or similar structure to act as a key-way in the core of the coil for engaging the winding head and ensuring a firm engaging connection between the winding head and the core of the coil to provide firm winding engagement of the coil. It has been found that sometimes the staple is pushed out of correct position by inserting the winding head or else is torn out of its engagement by turning of the winding head therein, which, without said engagement, the coil was not wound and thus the matrix was not tightened on the tooth.

SUMMARY OF THE INVENTION

The present invention is drawn to an improved winding tool which prevents the propellering action described above, with plastic matrices with the improved tool being embodied with a self-contained means to prevent the propellering without requiring the dentist to hold the coil during unwinding with his or her finger in order to thus avoid the deformation and destruction of the plastic coil and matrix, and thereby adding to the tool's usefullness to the user. Notably, the steel matrix coil is sufficiently firm to resist said propellering in any of the winding tools.

The present invention is also drawn to a new configuration for the winding head which, rather than requiring a staple or similar engaging means inside the coil core, the winding head is provided with deep, sharp, uni-directional flutes for engaging the coil core. These flutes dig into the coil's core for positive non-slip engagement. The flutes create uni-directional notches in the coil from which the head is readily disengaged from the coil when the head is wound reversely. This improved head is compatible with the steel retainerless matrix coil as well.

The winding tool of the present invention can be used in conjunction with both the steel and the plastic matrix of the -299 patent and the -909 patent, and a new plastic matrix having additional improvements as disclosed in the inventor's copending application entitled Adjustable Plastic Film Matrix.

According to the present invention, a rotatably winding handle is co-rotatably engaged with an internal torque limiting barrel which is adjustably engaged with a rotatable flexible sleeve assembly which has a rotatable winding head at its terminal end for use in winding the plastic matrix coil, and disengaging from the said coil thereafter, with the tool having anti-propellering means in its internal shaft. The shaft is non-rotatably positioned in the core of the rotating tool, from its winding head socket to a user's palm grip, into which the multi-functional shaft is engaged against rotation by being anchored at the tool's opposite end to the palm grip. By holding the non-rotatable grip in the palm and turning the handle with the fingers of the same hand, the non-rotating shaft restricts the head against propellering during reverse winding of the head for coil disengagement which is readily completed thereby, without the destructive coil twisting.

The following describes other multi-functions of the shaft. In an enlarged axial bore through the barrel of the tool, the shaft underlies the coil which is bowed thereunder adding compression to the torque means, while additionally, the shaft is fitted with an enlargement collar to rest internally in a further enlarged axial space provided in the barrel to retain the barrel's axial relationship to the shaft as the barrel rotates over the shaft. Other functions are hereinafter covered. The enlargements are more fully described hereinafter.

Unlike the inflexible short internally floating shaft of the -905 patent, the shaft of this invention is non-floating, is flexible and is substantially the length of the tool and is anchored against rotation to the palm grip which, in the dentist's hand, prevents the propellering without need to press a finger against the coil during reverse winding for removal of the head from the coil. The dual torque means is comprised in part by a coiled spring which compresses a steel ball into a socket in the handle. The spring is compressed by the compression transmitting shaft as the shaft passes under and supports the spring, with the spring pressure causing the shaft to bow. The bowing contributes to the compression of the ball in the handle sockets for creation of the torque limitation. A set screw adjustably sets the torque limitation on the shaft which is required for each setting. A smaller handle socket provides a lower torque for plastic matrices, while the other socket permits the higher torque limitation for use with steel matrices. Torque limitation may be preset at the factory or by the user. To select a torque setting, the palm grip is held while the handle is telescoped axially either in or out of the palm grip, which axially shifts the handle over the internal barrel containing the dual torque limiting means. The torque means has the ball, and the handle has two sets of sockets radially positioned through its outer surface. The handle The handle has an axial bore for containing the torque limitor barrel. The barrel and handle are co-rotational when the ball of the barrel is compressed into the handle socket and the handle is rotated. Note: the ball slips out of engagement with the handle's sockets when the force used to rotate the handle is greater than the torque limitation setting. The handle is telescopically moved over the barrel when neither are rotating, to axially shift the handle's sockets ball-engagement to either high or low limit sockets in the handle, as required by the user. Thus the compression transmitting shaft acts to provide the tool with compression on the ball, as well as non-rotational anti-propellering means without requiring finger pressure to prevent propellering on a plastic matrix. Notably, the short rigid floating shaft of the -909 patent with its handle being devoid of a non-rotatable palm grip anchored to a full length non-rotatable shaft, was one of the significant causes for said propellering. It is notable that in the tool of the present invention, the palm grip and shaft are anchored together and are not rotatable, while the winding head, the flexible sleeve, and the torque limitor barrel all bearingly rotate over the stationery, non-rotatable shaft when the ball-engaged handle is rotated in either direction. In none of inventor's previous tool inventions does a compression transmitting shaft exist for transmitting adjustable torque limitation to a matrix while said shaft protects the matrix from destructive propellering forces.

Another advantageous feature of the invention is the provision, in the handle, of a rotatable torque limitor barrel which carries the flexible sleeve on its exposed end and through which the non-rotatable shaft extends, and which barrel's bore includes two different bore enlargements, one containing said limitor bearing on said shaft, the other containing and axially fixing therein an offset or enlarged portion of the shaft. The handle can be moved to either of two separate torque limiting locations by shifting the handle axially over the torque barrel. Torque transmitting limiting means are engaged between the barrel and the handle for applying either of two discrete torque-limitations to the handle as the handle is rotated. The limitation causes the limitor ball to slip out of the handle's socket when torque is excessive. The offset or enlargement of the shaft maintains the correct axial position of the non-rotating shaft with the rotating barrel despite the fact that the handle is routinely moved axially over the barrel for the selction of the desired dual torque limiting handle socket.

According to another advantageous feature of the invention, the winding head is provided with deep flutes having sharp edges. The winding head is also conical in form. In this way shallow slits or cuts are made in the coil core, at least at the entry end of the coil core. These fold back flaps of material which then engage against sides of the flutes to achieve a firm, unidirectional engagement between the winding head and the coil. The coil can thus be securely and tightly wound to tighten the matrix. At the same time this configuration for the winding head permits it to be easily extricated from the coil when rotated in an opposite direction.

A still further object of the present invention is to provide an improved, preferably dual torque limiting and winding tool which is simple in design to use, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a side perspective view of the improved dual torque winding tool of the present invention;

FIG. 2 is a side elevational view of the internal spring-like shaft which avoids the propellering action according to the present invention;

FIG. 3 is a view similar to FIG. 2 showing another preferred embodiment of the internal shaft;

FIG. 4 is a side prespective view of the palm grip and part of the internal shaft of the present invention;

FIG. 5 is a partial, axial sectional view, partly in elevation of the winding tool of FIG. 1;

FIG. 6 is a partial, side elevational view, partly in section of the winding tool of FIG. 1, shown in an enlarged scale:

FIG. 7 is a radial sectional view taken along the lines 7—7 of FIG. 5;

FIG. 8 is a perspective view showing the prior winding tool and illustrating the undesirable propellering effect;

FIG. 9 is a perspective view showing how the prior winding tool deforms and fails to disengage the unwinding head from the coil of a plastic matrix due to the propellering effect;

FIG. 10 is a perspective view showing the barrel construction for the dual torque apparatus of the winding tool of FIG. 1;

FIG. 11 is a perspective view which is similar to FIG. 9 but which shows how the present invention prevents the propellering effect and permits an easy removal of the winding head from the winding coil;

FIG. 12 is a partial axial sectional view of the preferred non-rotatable palm grip and part of the rotatable handle of an alternate embodiment of the invention;

FIG. 13 is a partial perspective view showing a preferred alternate embodiment for a flexible sleeve collar for connecting a flexible sleeve to the barrel of a winding tool in accordance with the invention;

FIG. 14 is a partial axial sectional view with parts in elevation showing the collar sleeve of FIG. 13 in a barrel of the present invention:

FIG. 15 is a radial sectional view of the collar shown in FIG. 13;

DESCRIPTION OF THE PREFERRED EMBODIMENTS

Figure 16:
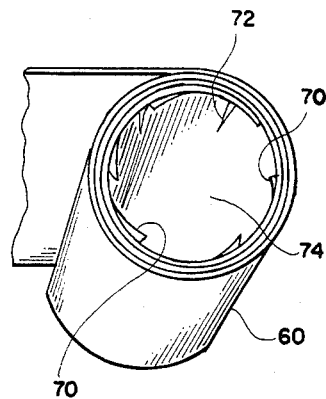
FIG. 16 is a perspective view, on an enlarged scale, showing a winding head having deep sharp edged flutes used for cuttingly engaging in the plastic coil for winding the coil of a matrix made in accordance with the above-identified co-pending application.

Referring to the drawings in particular, the invention embodied therein in FIG. 1 comprises a winding tool having a rotatable winding handle 20 which is rotatable by a dentist to rotate a bent flexible sleeve 4 which in turn rotates a winding head collet 2. A winding head or member 9 which is fixed to the collet is thus rotated. The winding head is used to wind the coil of a retainerless dental matrix disclosed in the patents identified above.

A non-rotatable palm grip 30 or 30a is telescopically mounted over the rotatable finger-driven handle. A non-rotatable shaft and a barrel are mounted in a bore of the handle. The non-rotatable shaft is anchored inside a bore in the non-rotatable palm grip for providing the anti-propellering effect when said grip is held by a user. In operation, and as illustrated in FIG. 11 the palm grip 30 can be held in the palm of the hand, while the fingers of that hand are used to rotate the handle 20. FIG. 11 also shows how the handle 20 can be rotated in a counter-clockwise direction for disengaging the winding head 9 from a winding coil 60 without propellering or twisting the reversely winding coil or damaging the matrix 62 connected to the winding coil. The anti-propellering mechanism which permits the operation shown in FIG. 11 includes, as shown in FIGS. 2, 4 and 5, the non-rotatable shaft 40 which is made of spring-like resilient material. Shaft 40 includes a bent end 40a which is received within the rotatable flexible shaft 4 as shown in FIG. 6 to maintain the bent contra angled shape of the flexible shaft.

It is noted that the non-rotatable shaft is anchored to and restrained against propellering by the hand-held palm grip. Everything else rotates.

Figure 18:
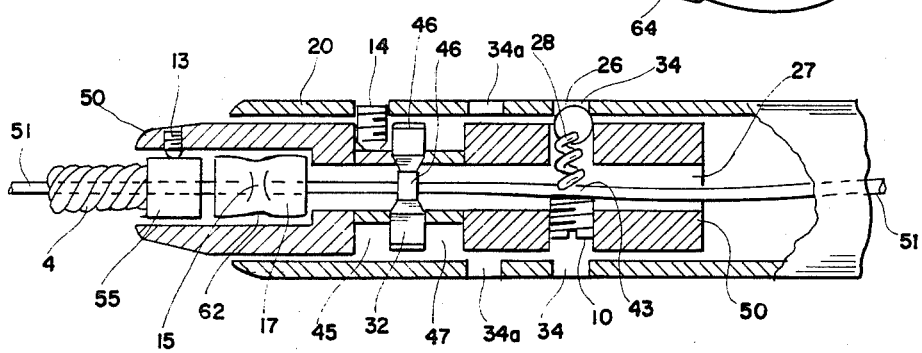
FIG. 18 is a partial sectional view of the barrel showing in particular the shaft collar positioned inside the barrel's shaft-enlargement area in the bore space of the barrel.

As also visible in FIGS. 2, 5 and 6, shaft 40 includes an offset or enlarged loop 6 while FIGS. 3 and 18 show similarly functional shaft enlargements. The opposite end of shaft 40 carries a flat area 40b which, as shown in FIG. 4, can be engaged by a set screw 8 threaded into the palm grip 30 to fix the shaft 40 against rotation with the non-rotatable grip 30 which is held in the user's hand.

FIGS. 4 and 5 also illustrated a probe portion 5 which is formed as one piece with the grip 30 and which extends into the handle 20. Probe 5 includes a probe bore 29 through which the end of shaft 40 extends.

As best illustrated in FIGS. 5, 7 and 10 the dual torque mechanism of the winding tool comprises a one piece barrel 50 which is mounted within the bore or space 41 of the handle 20. Barrel 50 includes an axially extending barrel bore 27 through which the shaft 40 extends, and at least one radially extending ball bore 37 which communicates with the barrel bore 27. A ball 26 is mounted for radial movement in the ball bore 37 and is biased outwardly by both a compression spring 28 and the bowed shaft 40 or 51 at bow 43. As shown in FIG. 7, the upper end of compression spring 28 is shaped to cup the ball 26 and urge it into engagement with a ball socket 34 of the handle 20. The lower end of spring 28 forms a curved seat for engaging on the shaft 40. This urges and bows shaft 40 against coil spring 28 and onto a compression set screw 10 which is threaded into the barrel 50. Another diametrically opposite socket 34 provides access for a screwdriver for tightening or loosening the set screw 10. In accordance with the dual torque mechanism of the inventor's prior dual torque winding tool invention, the tension of spring 28 is set by set screw 10 up until a certain torque limiting value which is applied by handle rotation 20 on barrel 50, the handle and barrel will co-rotate. However, as the winding coil tightens the matrix on the tooth, the matrix resists further tightening of the coil which causes the ball in the dual torque to slip out of its engagement with the barrel, with continuing rotation of the handle causing the ball to repeatedly slip from one handle socket to the next causing a sonic click which tells the dentist that the matrix is fully tightened at which time he stops further rotation of the handle. When the ball slips out of the socket engagements the barrel stops rotation despite continued rotation of the handle. This is torque control working. This clicking sound is an audible signal to the dentist to stop turning the handle 20. The correct amount of torque is thus supplied to the winding coil of the matrix. This torque limitation is particularly important for plastic matrices since too much torque would destroy the coil and render the matrix useless. It is also important for metal matrices but the torque can be higher in this case. To provide a dual torque capacity, the handle 20 is telescoped into palm grip 30a in the axial direction over the barrel, while gripping the palm grip so that the limitor ball can engage a second set of ball sockets shown for example at 34a in FIG. 5 which is of a different diameter. Notable, the same ball engaged in a larger diameter handle socket requires increased torque for disengagement of said ball from said socket, as for winding the steel coil, in which case the torque limitator permits higher torque with use of said larger socket.

So that the barrel will rotate up to a different torque limitation when the ball 26 is engaged with the handle's other ball socket 34a, the other ball socket can have a different diameter or different contour so that the ball disengages under a different torque condition. Torque load and limitation is determined by four factors, acting with each other. That is: socket diameter; ball compression from coil spring; compression from bowed shaft; and torque limiting/setting screw.

In order to permit the barrel 50 with its connected flexible sleeve 4 and the winding head 9 to rotate while the shaft 40 is held against rotation and propellering, the bent shaft end 40b is nonrotatably anchored inside the bore of palm grip 30a with set screw 8 as in FIG. 12. The dentist grasps the palm grip 30a which fixedly holds the entire shaft against rotation, thereby preventing propellering.

To position the ball 26 into the desired high or low torque socket of the handle and retain the axial position of the barrel 50, barrel 50 is provided with an escapement 32 as best shown in FIG. 10, and FIG. 18 where a guide screw 14 traverses through slots 46 which receive said screw 14 which is threaded inwardly from the handle 20 and into either high or low channels 47 or 45. During the co-rotation of the handle and barrel having escapement 32, axial movement of handle 20 is precluded by the presence of set screw 14, in said channels. Handle 20 can only be moved axially to change torque limiting socket-to-ball engagement when one of the slots of escapement 32 are aligned with the set screw 14 which occurs only when the handle is not rotating.

FIG. 12 shows an embodiment of the invention where the handle includes a probe portion 20a for receiving a length of the shaft 40 and for insertion into a space 33 of the modified palm grip 30a. Again a set screw 8 fixes the end of the shaft 40 to the grip.

Turning once more to FIGS. 5 and 6, a threaded collar 18 is fixed to one end of the flexible sleeve 4. The other end of flexible sleeve 4 carries the collet 2. Collet 2 has a blind bore or socket 23 for receiving the end of shaft 40. To engage the shaft 40 and the flexible sleeve 4 into the handle and barrel arrangement 20, 50, collar 18 is threaded into a barrel thread 19 of barrel 50. This threading operation continues until the end of shaft 40 (at bent portion 40a) is fully seated in the socket 23. The threads of collar 18 or the threads 19 may be provided with a thread locking adhesive before collar 18 is threaded onto barrel 50 to fix the relative position between the flexible sleeve 4 and the barrel 50.

To ensure that the shaft 51 does not axially move out from the torque barrel 50 and thereby disengage shaft 51 from the socket 23, the shaft 51 is provided with a fixed shaft collar 17 or enlargement which is seated within an enlargement 52 of the bore 27 in the barrel 50. Shaft collar 16 and shaft 51 are thereby maintained in an axially fixed position in the barrel 50 within the space 52.

FIG. 3 shows an alternate embodiment of the shaft enlargement, this shaft labelled 40, which carries a loop 6. Shaft loop 6 can be seated within the space 52 of barrel 50.

FIGS. 13 through 15 illustrated a modified form for the flexible sleeve collar, this time number 55, which avoids the rather more expensive threading requirement of threaded collar 18. Collar 55 is provided with an axial slot 57 which receives a set screw 35 threaded near the end of barrel 50. As shown in FIGS. 13 and 15, the flexible sleeve 4 is fixed to the slotted collar 55, with set screw 35.

Slot 57 permits an adjustable axial positioned during tool assembly of collar 55 in the end of barrel 50 again to seat the end of shaft 40 in the blind bore 23 of the winding head collet 2. Collar set screw 35 is then tightened into slot 57 to fix the axial position of the collar 55.

To select one of the two torque limiting sockets provided in said handle, it is noted that with the anchoring of the opposite end of shaft 51 in palm grip 30, 30a, the palm grip is held in one hand while the handle is shifted axially over the barrel to telescopically enter or retract the handle from the palm grip. Thus the barrel's ball will engage either the high or low torque limiting sockets.

Notably, the shaft is multi-functional with its bend at the flexible sleeve; its novel collar 17 enlargement in the barrel area 52 of FIG. 18 and its anchorage in the palm grip, which telescopically receives the rotatable tool driving handle. The shaft is the means which links all of the dual torques components in the barrel while serving to retain said shaft's axial alignment in the flexible sleeve during the rotary winding action and the axial shifting of the handle over the barrel when the handle is shifted to switch the barrel's ball from the handle's low-to-high torque limiting sockets or the reverse thereof. The elongated non-rotary shaft and its functional connections with all the other components and the palm grip provide the tool with propellering prevention of a plastic retainerless matrix.

Figure 17A:
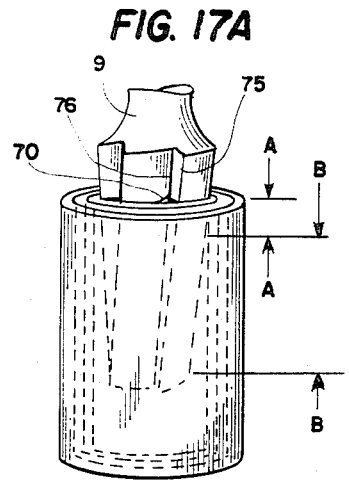
FIG. 17a is a perspective view on an enlarged scale showing the sharp fluted head inside a coil, illustrating that the conical head can only slash and engage into the topmost portion of the relatively straight-sided coil core.
Figure 17:
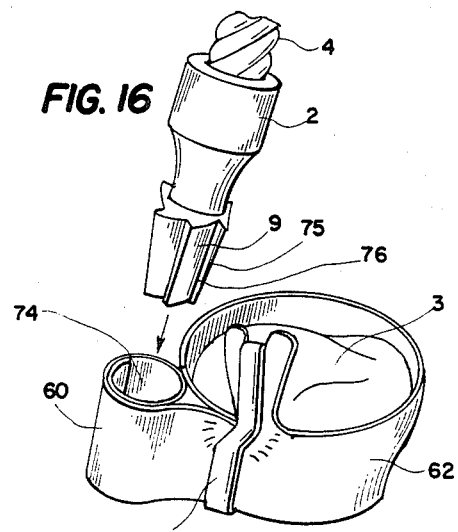
FIG. 17 is a perspective view showing how the winding coil of a plastic matrix has been cut into and modified by the sharp fluted winding head of FIG. 16 to improve the manner in which it is engaged and wound by the winding head.

Turning now to FIGS. 16, 17 and 17a, the present invention also includes an improved winding head 9 which is fixed to the collet 2 which in turn is fixed to the flexible sleeve 4. Winding head 9 has a cross section in the form of a unidirectional fluted star-like formation with sharpened flute edges 75. Each flute has a seat edge 76. The distance between edges 75 and 76 is relatively deep. The winding head also tapers in the form of a truncated cone. Winding head 9 is insertable into the inner core diameter 74 of a winding coil 60 to slashingly engage rotate the windable coil causing it to wind and tighten around the winding head 9 and to draw material from the matrix 62, under the lock loop 64 and onto the coil 60. As known from the inventor's previous patents concerning the retainerless matrix, this serves to lock the coil 60 against the lock loop 64 which locks the matrix 62 around a tooth 3.

The effect of the sharpened edges 75 of the uni-directional fluted winding head 9 is to cut core minute slashes 72 into the upper entry end of the coil 60 in the inner core diameter 74 of the coil. The slashes are of a set depth due to said head 9 conical shape which can cut no deeper than shown in FIG. 17a between A—A area. The B—B area is not slashed. This slash forms raised engaging edges 70 which engage against the flutes area 76 of the fluted winding head 9. The provision of deep set depth for each of the flutes of the fluted winding head 9 assures sufficient engagable slash depth 72, while flute depth point 76 avoids too deep a cut for the slashes 72. It also has been found that the uni-directional slashes 72 permit a free disengagement of the head 9 from the coil core 74 when the head 9 is rotated in an opposite disengaging direction, from the engaging and tightening direction.

The maximum diameter of the conical winding head 9, at its top, is selected to be greater than the inside diameter matrix of the coil core 74 so that the slashes 72 are formed only at the top of the smaller diametered core, which is relatively straight-sided compared to the conical winding head, which engages said coil core only at the core's entry point.

While specific embodiments of the invention have been shown and described in detail to illustrate the application of the principles of the invention, it will be understood that the invention may be embodied otherwise without departing from such principles.

What is claimed is:

1. A torque limiting and winding tool for winding a coil of one of a plastic and a metal retainerless matrix, comprising: a rotatable handle having a handle bore therein; a barrel mounted in said handle bore; torque limiting means mounted to said barrel for engagement with said handle to establish a co-rotational engagement between said barrel and said handle up to an adjustable torque limit beyond which said handle is disengaged from said barrel and rotates independently of said barrel; adjustable compression means for applying an adjustable force against said torque limiting means to adjust the torque limit at which said handle becomes disengaged from said barrel; a flexible sleeve connected to said barrel for co-rotation with said barrel, said flexible sleeve extending out of said barrel; a winding head fixed to said flexible sleeve for rotation with said sleeve and for engaging a coil of a retainerless dental matrix to wind the coil; a palm grip connected to said handle for relative rotation between said palm grip and said handle whereby said palm grip is held in the hand of a user while the fingers of the hand can be used to rotate said handle; a bendable, nonrotatable shaft made of flexible and resilient material, extending through said handle bore and through said barrel, said shaft having a bent end extending into said flexible sleeve for maintaining a bent shape for said flexible sleeve, said shaft being anchored to said grip for nonrotation of said shaft with nonrotation of said grip, said handle, barrel, flexible sleeve and winding head being rotatable together while said shaft is nonrotatable for avoiding a propellering movement of said bent flexible shaft, said shaft being operatively engaged with said adjustable compression means for applying reciprocal compression to said torque limiting means by virtue of the resiliency of said shaft; said shaft being operatively engaged with said adjustable compression means so as to permit rotation of said barrel, said torque limiting means and said adjustable compression means around said shaft, said shaft receiving a bow under the influence of said adjustable compression means.

2. A tool according to claim 1, wherein said barrel is mounted for rotation and for axial movement in said handle bore of said handle, said barrel having a barrel bore therethrough, said shaft extending through said handle and said barrel bores, said bow in said shaft being engaged and formed between said torque limiting means and said compression means.

3. A tool according to claim 2, wherein said barrel includes a ball bore intersecting said barrel bore, said handle including at least one ball socket for receiving a ball, said torque limiting means comprising a ball movably mounted in said ball bore and into engagement with said ball socket and a spring disposed in said ball bore and engaged against said ball, said spring being engaged with said shaft and forming said bow in said shaft, said compression means comprising a set screw engagable against said shaft and against said spring.

4. A tool according to claim 1, wherein said compression means includes a set screw for adjusting compression pressure on said torque limiting means, said shaft of flexibly resilient material to provide compression transmittability to said torque limiting means, sufficient to givingly respond to compression pressure from said set screw.

5. A tool according to claim 1 wherein said barrel has a barrel bore therethrough, said compression means and said torque limiting means being at least partly in said barrel bore, said barrel bore having a diameter which is larger than a diameter of said shaft for accomodating said bow of said shaft with rotation of said barrel with respect to said shaft.

6. A tool according to claim 2, wherein said palm grip includes a palm bore for receiving said shaft, said palm bore being of a smaller diameter than said barrel bore, and said handle bore.

7. A tool according to claim 3, wherein said spring has one end which is cupped for receiving said ball and an opposite end which is shaped for axially engaging over said compression transmitting shaft for permitting relative rotation of said shaft between said spring, and said set screw as said spring rotates over said non-rotating shaft.

8. A tool according to claim 7, wherein said set screw is threaded in said ball bore for urging said bowed compression transmitting flexible shaft against said spring by an adjustable amount.

9. A tool according to claim 2, wherein said barrel bore includes an enlarged diametric portion, forming a shoulder therein said shaft having an enlargement seated against said shoulder in said enlarged portion of said barrel bore for holding said shaft in an axial fixed position with respect to said barrel, with said bore end opposite said shoulder in said enlarged bore space being enclosed by a collar on said flexible sleeve which encloses said shaft enlargement within said space and against axial displacement of said barrel with said shaft.

10. A tool according to claim 9, wherein said enlargement of said shaft comprises a loop in said shaft.

11. A tool according to claim 9, wherein said enlargement of said shaft comprises a collar axially fixed on said shaft.

12. A tool according to claim 9, including a collar fixed to an end of said flexible sleeve with said collar fixable at an axially adjustable position to said barrel.

13. A tool according to claim 12, wherein said sleeve collar engages against said enlarged portion of said shaft to retain said enlarged portion of said shaft within said enlarged portion of said barrel bore.

14. A tool according to claim 13, wherein said collar is threaded to said barrel.

15. A tool according to claim 13, wherein said collar includes an axially extending slot, and a collar set screw threaded to said bore and engaged into said slot for holding said collar at an adjustably fixed axial position with respect to said barrel.

16. A tool according to claim 2, wherein said palm grip includes a probe extending into said handle bore and axially movable in said handle bore with said shaft and with said barrel.

17. A winding tool for winding a coil of a retainerless dental matrix comprising:
a rotatable handle having a handle bore therein;
a rotatable flexible sleeve operatively connected to said rotatable barrel for rotation with said handle;
a non-rotatable shaft having a bent end extending into said flexible sleeve for holding said flexible sleeve in a bent shape, said shaft being held from rotation with respect to said handle and said sleeve; and
a winding head fixed to said flexible sleeve and rotatable with said flexible sleeve, said winding head having a star-shaped cross section with a purality of unidirectional deep flutes each having a raised cutting edge and a base edge spaced from said raised cutting edge for partly cutting into and then engaging the core of a coil of a retainerless dental matrix, for winding of said coil.

18. A tool according to claim 17, wherein said winding head is conical having a large diameter portion adjacent said flexible sleeve.

19. A tool according to claim 18, including a barrel having a barrel bore therethrough for receiving said shaft and mounted for rotation and for axial movement in said handle, and bowing means engaged between said barrel and said shaft for placing a bow in said shaft.

20. A tool according to claim 19, including a non-rotatable palm grip anchoringly fixed against rotation to said shaft for axial telescopic movement of said handle into said grip.

* * * * *